(12) United States Patent
Chuang et al.

(10) Patent No.: US 8,271,075 B2
(45) Date of Patent: Sep. 18, 2012

(54) AUDIO HEADSET WITH BIO-SIGNAL SENSORS

(75) Inventors: Cheng-I Chuang, San Jose, CA (US); KooHyoung Lee, Sunnyvale, CA (US)

(73) Assignee: NeuroSky, Inc., San Jose, CA (US)

( * ) Notice: Subject to any disclaimer, the term of this patent is extended or adjusted under 35 U.S.C. 154(b) by 533 days.

(21) Appl. No.: 12/378,156

(22) Filed: Feb. 10, 2009

(65) Prior Publication Data

US 2009/0214060 A1 Aug. 27, 2009

Related U.S. Application Data

(60) Provisional application No. 61/028,258, filed on Feb. 13, 2008.

(51) Int. Cl.
*H04R 25/00* (2006.01)
*A61B 5/0476* (2006.01)

(52) U.S. Cl. ............ 600/544; 600/383; 600/559

(58) Field of Classification Search ........... 600/544, 600/383, 559
See application file for complete search history.

(56) References Cited

U.S. PATENT DOCUMENTS

| | | | | |
|---|---|---|---|---|
| 4,610,259 A | | 9/1986 | Cohen et al. | |
| 4,924,502 A | * | 5/1990 | Allen et al. | 381/72 |
| 4,955,388 A | | 9/1990 | Silberstein | |
| 5,339,826 A | | 8/1994 | Schmidt et al. | |
| 5,495,853 A | * | 3/1996 | Yasushi | 600/545 |
| 5,740,812 A | * | 4/1998 | Cowan | 600/545 |
| 5,844,824 A | * | 12/1998 | Newman et al. | 345/156 |
| 5,954,667 A | * | 9/1999 | Finkenzeller et al. | 600/544 |
| 5,983,129 A | * | 11/1999 | Cowan et al. | 600/544 |
| 6,001,065 A | | 12/1999 | DeVito | |
| 6,154,669 A | * | 11/2000 | Hunter et al. | 600/383 |
| 6,254,536 B1 | | 7/2001 | DeVito | |
| 6,296,543 B1 | | 10/2001 | Andrews | |
| 6,381,481 B1 | * | 4/2002 | Levendowski et al. | 600/383 |
| 6,574,513 B1 | * | 6/2003 | Collura et al. | 607/122 |
| 6,640,122 B2 | * | 10/2003 | Manoli et al. | 600/383 |
| 6,694,180 B1 | | 2/2004 | Boesen | |
| 7,128,577 B2 | | 10/2006 | Renaud | |
| 7,197,350 B2 | * | 3/2007 | Kopke | 600/383 |
| 7,433,718 B2 | * | 10/2008 | Manabe et al. | 455/575.1 |
| 7,689,274 B2 | * | 3/2010 | Mullen et al. | 600/544 |
| 2004/0073129 A1 | * | 4/2004 | Caldwell et al. | 600/544 |
| 2004/0097824 A1 | | 5/2004 | Kageyama | |
| 2004/0252103 A1 | | 12/2004 | Bonnat | |
| 2007/0066914 A1 | | 3/2007 | Le et al. | |
| 2007/0106169 A1 | * | 5/2007 | Fadem | 600/544 |
| 2007/0112277 A1 | * | 5/2007 | Fischer et al. | 600/544 |
| 2007/0173733 A1 | | 7/2007 | Le et al. | |
| 2007/0191727 A1 | * | 8/2007 | Fadem | 600/544 |

(Continued)

OTHER PUBLICATIONS

Fingelkurts et al., The Regularities of the Discrete Nature of Multi-Variability of EEG Special Patterns, International Journal of Psychophysiology 47, 2003, pp. 23-41.

(Continued)

*Primary Examiner* — Ha Tran T Nguyen
*Assistant Examiner* — Jordan Klein
(74) *Attorney, Agent, or Firm* — Van Pelt, Yi & James LLP

(57) ABSTRACT

An audio headset with bio-signal sensors is provided. In some embodiments, an audio headset that includes one or more electroencephalography (EEG) sensors is provided.

12 Claims, 6 Drawing Sheets

U.S. PATENT DOCUMENTS

2007/0207858 A1* 9/2007 Breving .......................... 463/36

OTHER PUBLICATIONS

Kaplan et al., Probability Patterns of the Human EEG Narrow-Band Differential Spectra During Memory Processes, Human Physiology, vol. 24, No. 4, 1998.

Kaplan et al., Application of the Change-Point Analysis to the Investigation of the Brains's Electrical Activity, Chapter 7 in Brodsky et al., Nonparametric Statistical Diagnosis: Problems and Methods, pp. 333-388, 2000.

Borisov et al., Analysis of EEG Structural Synchrony in Adolescents with Schizophrenic Disorders, Jun. 7, 2004.

A. Kaplan, The Problem of Segmental Description of Human Electoencephalogram, Mar. 18, 1998.

Landa et al., A Model for the Speed of Memory Retieval, Published Oct. 21, 2003.

Levichkina et al., Unconscious Context Control of Visual Perception of Simple Stimuli: A Study Using Evoked Potentials, Aug. 2, 2007.

Kaplan et al., Unconscious Operant Conditioning in the Paradigm of Brain-Computer Interface Based on Color Perception, Jun. 29, 2004.

Kaplan et al., Macrostructural EEG Characterization Bases on NonParametric Change Point Segmentation: Application to Sleep Analysis, Jan. 8, 2001.

Shishkin et al., Combining the Extremities on the Basis of Separation: A New Approach to EEG/ERP Source Localization, Nov. 2004.

* cited by examiner

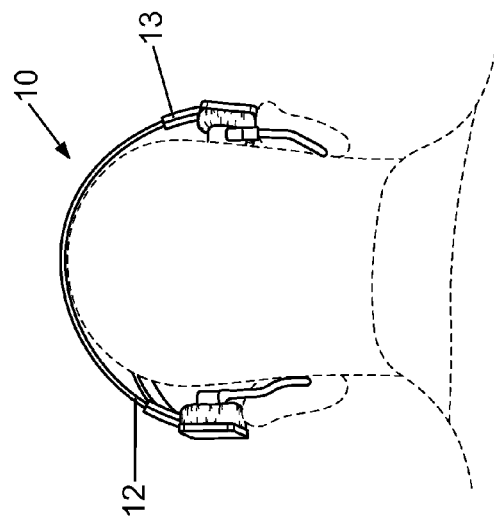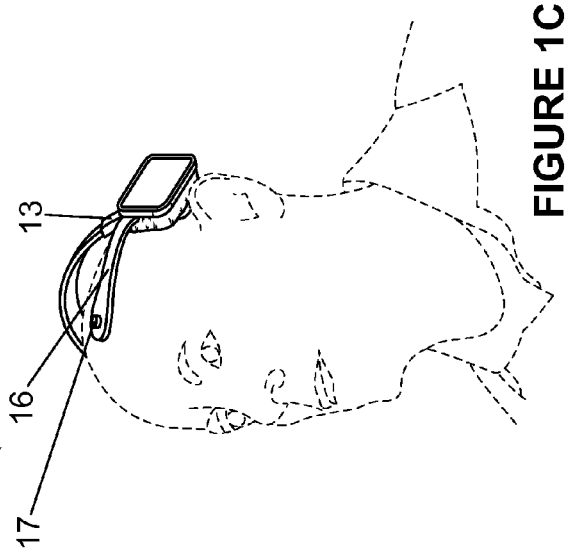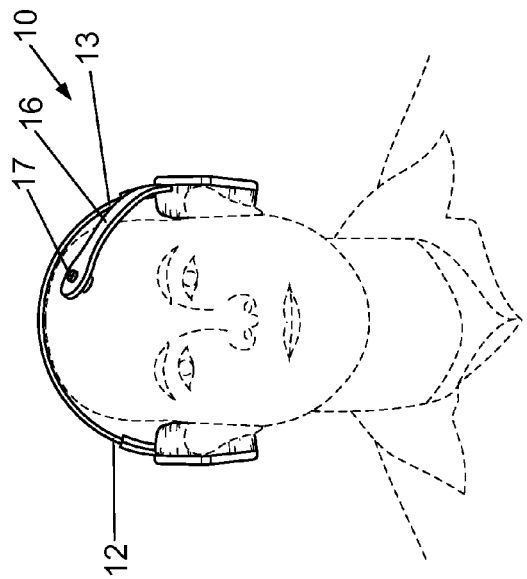

AUDIO HEADSET WITH BIO-SIGNAL SENSORS

CROSS REFERENCE TO OTHER APPLICATIONS

This application claims priority to U.S. Provisional Patent Application No. 61/028,258 entitled NEURO-HEADSET DEVICE WITH AUDIO SPEAKERS filed Feb. 13, 2008 which is incorporated herein by reference for all purposes.

BACKGROUND OF THE INVENTION

Typical headsets have audio speakers that channel sound to the user's ears or are sound cancelling devices. These typical headsets do not include one or more bio-signal sensors (e.g., EEG sensors that allow the brain waves of the user wearing the headset to be measured). Thus, it is desirable to provide an audio headset with one or more bio-signal sensors.

BRIEF DESCRIPTION OF THE DRAWINGS

Various embodiments of the invention are disclosed in the following detailed description and the accompanying drawings.

FIGS. 1A through 1C are diagrams illustrating a neuro-headset being worn by a user in accordance with some embodiments of the present invention.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

In some embodiments, the device as described herein is particularly applicable to an audio headset with bio-signal sensors (e.g., a neuro-headset with EEG sensors and over the ear headphones or earbud headphones), and it is in this context that the device will be described. It will be appreciated, however, that the device has greater utility, because, for example, the audio headset can be used with other types of sensors (such as other types of bio-signal sensors) inside of the earpieces of the headset (and/or otherwise located in connection with the headset) and/or other types of multimedia capabilities, such as audio/hearing bone conduction, headphone video head mounted display (e.g., video glasses with audio speakers) and/or 3D stereoscopic.

Figure 2:
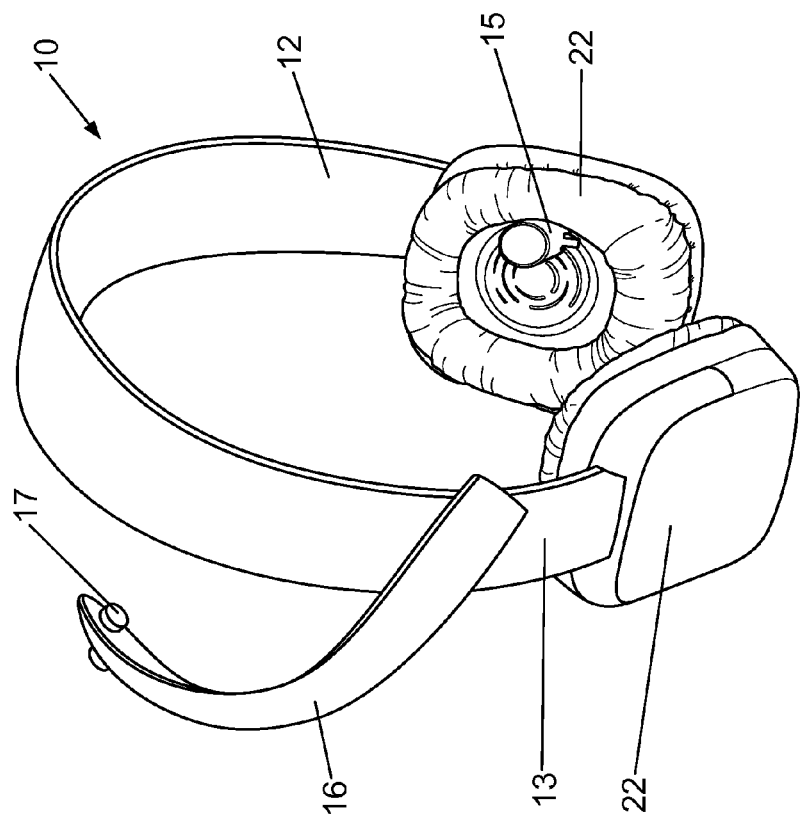
FIG. 2 illustrates a neuro-headset with audio speakers and EEG sensors in accordance with some embodiments of the present invention.
Figure 3:
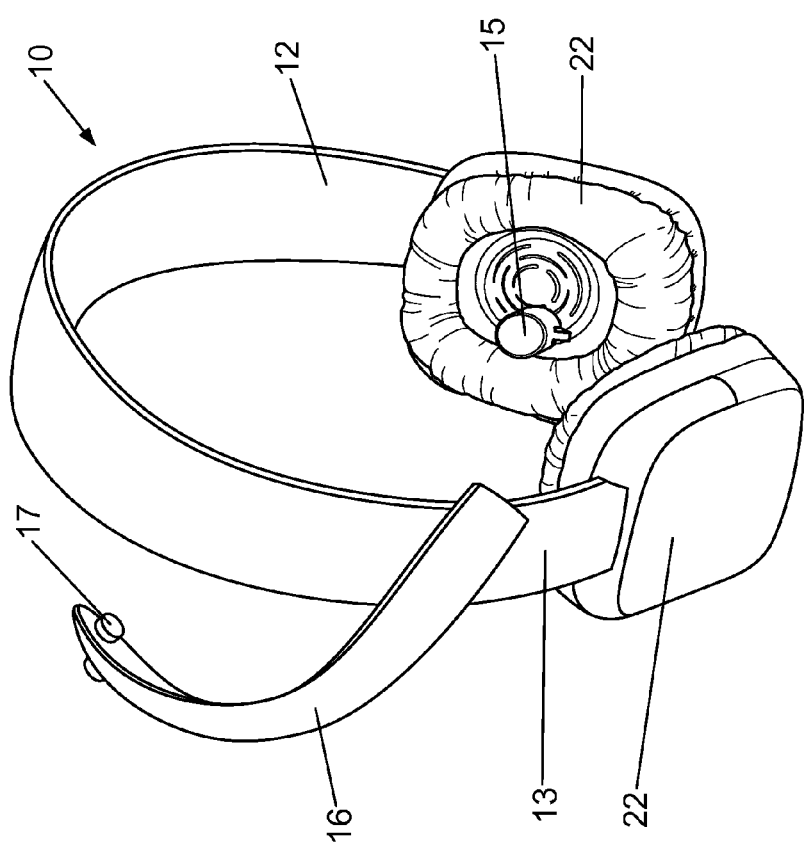
FIG. 3 illustrates a neuro-headset with audio speakers and EEG sensors in accordance with some embodiments of the present invention.

FIGS. 1A through 1C are diagrams illustrating a neuro-headset being worn by a user in accordance with some embodiments of the present invention. As shown, a neuro-headset 10 is being worn by a user who is shown in phantom in which a dashed outline is provided to depict the user in the diagrams. For example, the neuro-headset 10 can have first and second side portions 12, 13 that rest near the ears of the user and allow an electroencephalography (EEG) sensor 15 (e.g., as shown in FIGS. 2 and 3) to sit against the skin of the user behind the ear. The neuro-headset 10 also includes an arm portion 16 with an EEG sensor 17 located near the end of the arm portion 16, which, for example, can be used to position the EEG sensor on the forehead of the user. In some embodiments, two or more EEG sensors are provided in an earpiece of the neuro-headset 10. In some embodiments, EEG sensors are provided in each earpiece of the neuro-headset 10. In some embodiments, other types of bio-signal sensors are provided in one or both earpieces of the headset in place of or in addition to the EEG sensors. In some embodiments, the headset is a mono-headset, in which there is only one earpiece instead of two earpieces. For example, once the neuro-headset 10 is properly positioned on the head of the user, the brainwaves of the user can be measured based on the signals detected by the sensors 15, 17 as described in more detail in U.S. patent application Ser. No. 11/656,828, filed on Jan. 22, 2007 and entitled "Method and Apparatus for Quantitatively Evaluating Mental States Based on Brain Wave Signal Processing System," which is incorporated herein by reference.

FIG. 2 and FIG. 3 each illustrate embodiments of neuro-headsets with audio speakers and EEG sensors in accordance with some embodiments of the present invention. As shown, these embodiments of the neuro-headset 10 include both audio speakers and EEG sensors. For example, the neuro-headset 10 can have the first and second side portions 12, 13 and the arm portion 16 with the EEG sensor 17 as described above. The neuro-headset 10 can also have an earpiece/speaker portion 22 at the end of each side portion 12, 13 so that the earpiece portion, for example, fits over the ear of the user when the neuro-headset 10 is being worn by the user. As shown, the neuro-headset 10 includes the EEG sensor 15 within the earpiece portions 22. In some embodiments, EEG sensors are provided in each earpiece of the neuro-headset 10. Also, the EEG sensor 15 can be located at different locations within the earpiece portions 22 as shown in FIG. 2 and FIG. 3. In some embodiments, the EEG sensor 15 is supported with a flexible material to adapt to different users' head and ear shape and sizes, provide wearing comfort, while providing enough pressure to the ear surface to ensure proper contact. In some embodiments, each sensor includes a spring-loaded mechanism that acts as the flexible support material. In some embodiments, other types of flexible materials, such as a rubber sleeve with metallic spine as shown in FIG. 5, are utilized.

Figure 4:
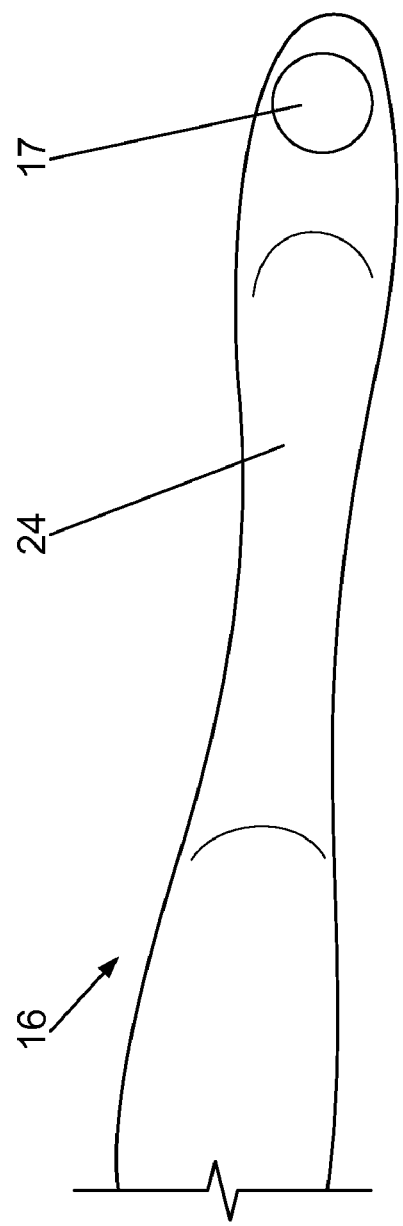
FIG. 4 illustrates a flexible arm portion of the neuro-headset with audio speakers and EEG sensors in accordance with some embodiments of the present invention.

FIG. 4 illustrates a flexible arm portion of the neuro-headset with audio speakers and EEG sensors in accordance with some embodiments of the present invention. As shown, the arm portion 16 (e.g., for each of the embodiments shown in FIGS. 2 and 3) includes a flexible portion 24 that allows the EEG sensor 17 to be more precisely positioned against the forehead of the user even with different head shapes and sizes of the user. For example, once the headset is properly positioned on the head of the user, it can be worn much like a normal headset with earpieces.

Figure 5:
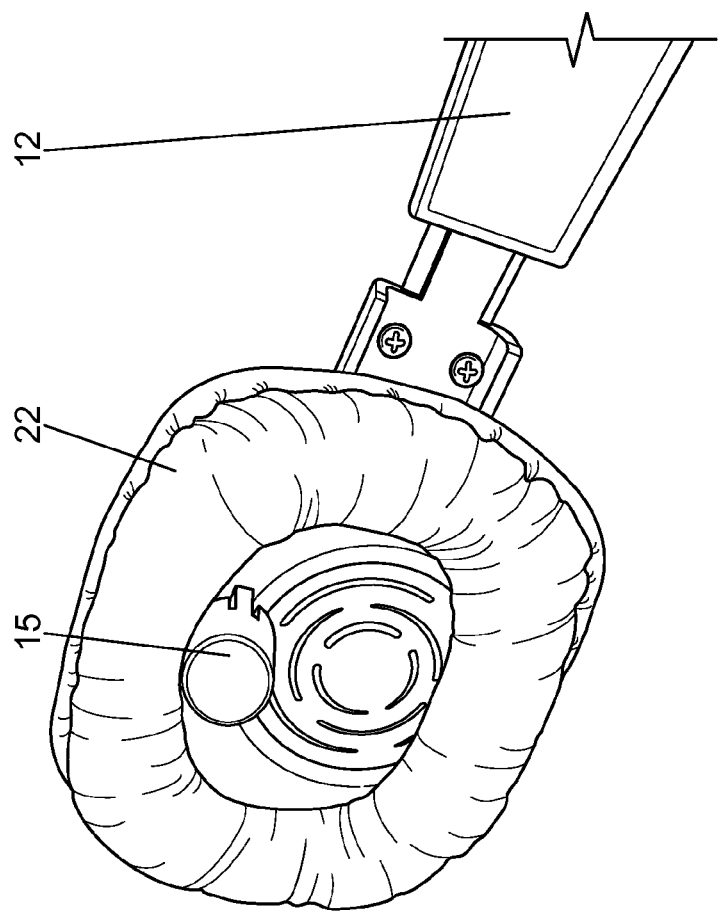
FIG. 5 illustrates an implementation of the earpiece of the neuro-headset with audio speakers and the EEG sensor in accordance with some embodiments of the present invention.

FIG. 5 illustrates an implementation of the earpiece of the neuro-headset with audio speakers and the EEG sensor in accordance with some embodiments of the present invention. As shown, the earpiece portion 22 (e.g., which can be padded for user comfort) includes the EEG sensor 15, which rests against the skin adjacent the user's ear when the headset is worn by the user, and which is able to sense the user's brainwave signals used for brainwave measurements. In some embodiments, such as the embodiments shown in FIGS. 2, 3 and 5, the EEG sensor 15 (also referred to as an electrode) is located in the earpiece of the headset so as to allow for contact with the preauricular skin area or helix or antihelix of the user's ear when the headset is worn by the user. In some embodiments, one or more of the EEG sensors are provided on the padded portion of the earpiece portion 22, and/or one or more of the EEG sensors are provided in the inner section of the earpiece portion 22 as shown.

Figure 6:
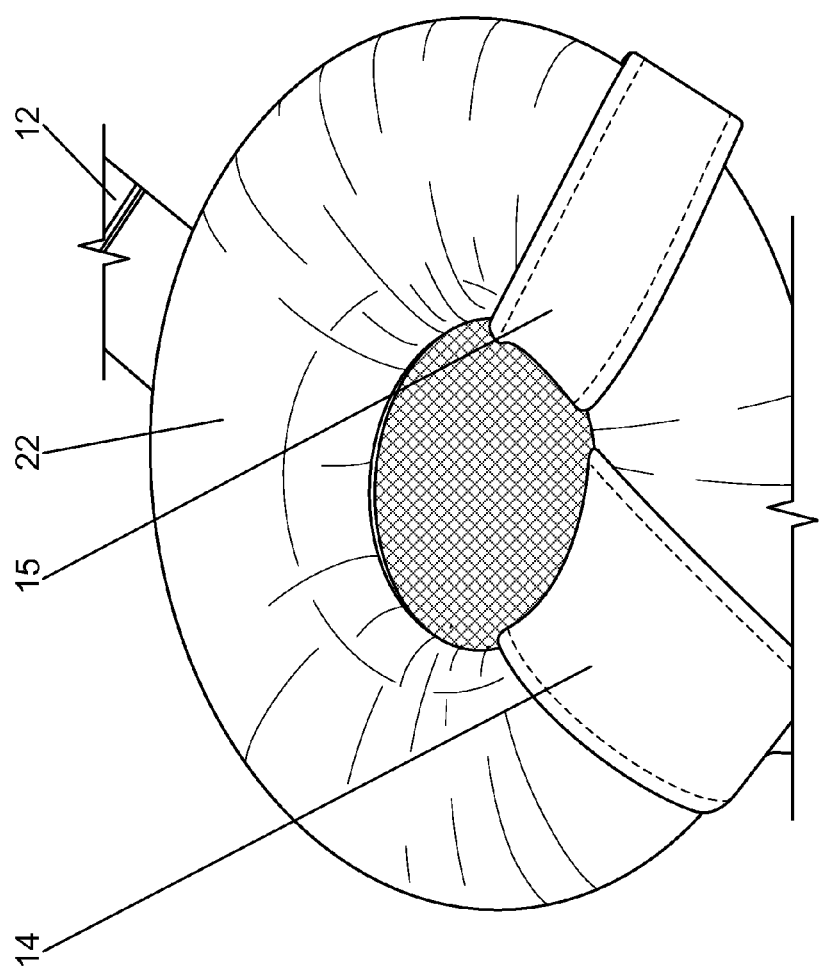
FIG. 6 illustrates an implementation of the earpiece of the neuro-headset with audio speakers and fabric EEG sensors in accordance with some embodiments of the present invention.

FIG. 6 illustrates an implementation of the earpiece of the neuro-headset with audio speakers and fabric EEG sensors (also referred to as fabric electrodes) in accordance with some embodiments of the present invention. As shown, the earpiece portion 22 (e.g., which can be padded for user comfort) includes two fabric EEG sensors 14, 15, which rest against the skin adjacent the user's ear when the headset is worn by the user, and which is able to sense the user's brainwave signals used for brainwave measurements.

In some embodiments, the headset and headset components shown in FIGS. 2 through 5 allow the EEG sensor(s) to be included discretely inside the ear piece(s) of an audio headset or earphone or headphone, which provides a simple to use, easy to wear, and easy to manufacture headset that is effective in sensing the EEG signals. In some embodiments, the device can be used with any headsets or earphones or headphone with earpiece(s) that enclose, or rest on the skin of wearer's ear(s) wherein one or more bio-signal electrodes are built inside the ear piece(s) to touch the skin of the wearer's ear.

In some embodiments, the bio-signal sensor(s) (e.g., EEG sensors and/or other types of bio-signal sensors) location and flexible support material allow for a headset and earphone design that can collect, for example, EEG signals effectively, while keeping the overall headset or earphone design essentially the same as the ones without an EEG sensor, which makes the headset or earphone simple to use, easy to wear and easy to manufacture. For example, the location of the EEG sensors in the earpieces of the headset as described herein can provide for effective signal detection in which the signals captured by such EEG sensors of the headset are comparable to the signals captured by a medical grade EEG sensor on, for example, a known BioPac MP150 system.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. An audio headset comprising:
a first side portion of the audio headset having a first earpiece attached to the first side portion so that the first earpiece can be placed on top of, over, or inside a user's ear when the audio headset is worn by the user; and
a first bio-signal sensor positioned inside of the first earpiece that is capable of resting against a skin portion of the ear of the user when the audio headset is worn by the user, wherein the first bio-signal sensor is a fabric electroencephalography (EEG) sensor comprising a strip of conductive fabric wrapped around a portion of the first earpiece for detecting brainwave signals, wherein the strip of conductive fabric includes a fabric EEG sensor and extends radially from a center of the inside of the earpiece to an edge of the earpiece.

2. The audio headset of claim 1, wherein the audio headset is a mono-headset.

3. The audio headset of claim 1, further comprising:
a second side portion of the audio headset having a second earpiece attached to the second side portion so that the first and second earpieces can be placed on top of, over, or inside a user's ears when the audio headset is worn by the user.

4. The audio headset of claim 1, further comprising:
a second side portion of the audio headset having a second earpiece attached to the second side portion so that the first and second earpieces can be placed on top of, over, or inside a user's ears when the audio headset is worn by the user; and
a second bio-signal sensor positioned inside of the second earpiece that is capable of resting against a skin portion of the ear of the user when the audio headset is worn by the user, wherein the second bio-signal sensor includes a fabric electroencephalography (EEG) sensor wrapped around a portion of the second earpiece for detecting brainwave signals.

5. The audio headset of claim 1, further comprising:
a second bio-signal sensor positioned inside of the first earpiece that is capable of resting against a skin portion of the ear of the user when the audio headset is worn by the user.

6. The audio headset of claim 1, further comprising:
an arm of the audio headset for holding a second bio-signal sensor that is capable of resting against a skin portion of a forehead of the user when the audio headset is worn by the user.

7. The audio headset of claim 1, further comprising:
a flexible arm of the audio headset holding a second bio-signal sensor that is capable of resting against a skin portion of a forehead of the user when the audio headset is worn by the user.

8. The audio headset of claim 1, wherein the first earpiece further comprises a flexible material inside of the first earpiece that supports the first bio-signal sensor and provides outward pressure.

9. The audio headset of claim 1, wherein the first bio-signal sensor is located on a padded portion of the first earpiece.

10. The audio headset of claim 1, wherein the first earpiece further comprises an over the ear headphone.

11. The audio headset of claim 1, wherein the first earpiece further comprises an audio bone conduction headphone.

12. The audio headset of claim 1, wherein the strip extends radially from the center of the inside of the earpiece at offset angles from a reference point and the offset angle is less than 180 degrees in either direction from the reference point.

* * * * *